US00PP17520P3

(12) United States Plant Patent
Recupero et al.

(10) Patent No.: US PP17,520 P3
(45) Date of Patent: Mar. 27, 2007

(54) YELLOW STAR SEEDLESS

(50) Latin Name: *Citrus limon*
Varietal Denomination: Yellow Star Seedless

(75) Inventors: Giuseppe Reforgisto Recupero, Acireale (IT); Giuseppe Russo, Acireale (IT); Santo Recupero, Acireale (IT)

(73) Assignee: Future Fruit, LLC, Visalia, CA (US)

( * ) Notice: Subject to any disclaimer, the term of this patent is extended or adjusted under 35 U.S.C. 154(b) by 0 days.

(21) Appl. No.: 11/041,066

(22) Filed: Jan. 21, 2005

(65) Prior Publication Data

US 2005/0166293 P1 Jul. 28, 2005

(51) Int. Cl.
*A01H 5/00* (2006.01)

(52) U.S. Cl. ..... Plt./201

(58) Field of Classification Search ..... Plt./201
See application file for complete search history.

(56) References Cited

PUBLICATIONS

Spiegel–Roy, Pinhas and Goldschmidt, Eliezer E., "Biology of Fruits," Cambridge University Press, 1996 (pp. 191–193).

*Primary Examiner*—Kent Bell
(74) *Attorney, Agent, or Firm*—Mark D. Miller

(57) ABSTRACT

A new and distinct variety of seedless lemon tree named 'Yellow Star Seedless' characterized by being a triploid, and having early bearing in August through to about January in the citrus areas of Sicily, Italy and Riverside, Calif. The tree has high yields and bears from year three onwards. The trees are highly tolerant to the Mal secco disease. The variety is further characterized by being genetically seedless. The fruit is well sized and has acceptable rind thickness, acid-sugar ratios and color. The skin has a smooth texture and the fruit stores well. The fruit has an average juice content of 30–40% at harvest. The fruit shape is typically ovoid.

7 Drawing Sheets

This application claims the benefit of European Union Community Plant Variety Office application Designation C-3869 (LEMOX), File Number 2004/0073 dated Jan. 22, 2004 a copy of which (with translation) is attached hereto and incorporated herein by this reference.

*Citrus limon.*

Variety denomination: 'Yellow Star Seedless'.

BACKGROUND OF THE NEW VARIETY

The present invention refers to a new variety of triploid lemon which will hereinafter be denominated as the 'Yellow Star Seedless' lemon tree. The 'Yellow Star Seedless' tree produces commercially seedless lemon fruit, bearing in late August through to March in the citrus areas of Sicily, Italy. The 'Yellow Star Seedless' plant is a triploid—having three sets of chromosomes. The trees bear from year three, and have consistent year-to-year bearing habits. The fruit has acceptable rind thickness, acid-sugar ratios and color, and has an average juice content of 30–40% at harvest.

In the development of new commercial fruit varieties, specific characteristics provide a premium on those fruit varieties that mature early or late in the growing season. For a new fruit variety to be a commercial success, the fruit must be of good size, good color, and also have good holding/storage. Advantageous harvest times and shipping characteristics are also important, as is the date the fruit matures. This new invention meets all of the aforementioned criteria and therefore would be of commercial appeal to the consumer.

The 'Yellow Star Seedless' variety is a triploid sexual hybrid. Polyploidy in citrus is well known (See pp. 191–193 of Speigel-Roy & Goldschmidt, 1996.) Citrus and related genera are typically diploidic and have two sets of 9 chromosomes (2n=18). Triploids, tetraploid and hexaploids exist naturally but occur in low percentages in the population. Citrus triploids are cytologically recognizable by the presence of an additional set of Chromosomes. In some cases, triploids are also morphologically recognizable.

ORIGIN AND ASEXUAL REPRODUCTION OF THE NEW VARIETY

The invention (variety) comprises a new and distinct variety of a seedless lemon plant named 'Yellow Star Seedless' discovered by the inventors in Azienda S Gregorio (RC), Sicily, Italy in 1999. The new invention is a triploid (3n=27 chromosomes) selection from sexual crosses made between a tetraploid (pollen) male parent ('Doppio Lentini' Lemon) and a diploid (seed bearing) female parent (*C.limon* (L.) Burm. femminello×'Pera del Commendatore') and called 'Yellow Star Seedless.' The new invention was subsequently asexually reproduced by the inventors in 2000 by bud grafting on to 'Sour Orange' root stock. The resulting trees were experimentally evaluated. The resulting tree growth was strong with no bud union abnormalities being noted on the 'Sour Orange' rootstock. An additional 10 trees were asexually reproduced by the inventors in 2003 by bud grafting on to 'Sour Orange' root stock and grown in Riverside, Calif. The inventors carefully compared all of the asexually reproduced trees with the originally discovered tree including the fruit and found, thus far, that they are identical in all respects. The instant tree reproduces true to type in successive generations of such asexual reproductions. The trees under evaluation are free from all known viruses and viroids including; *Tristeza, Exocortis, Xyloporosis and Psorosis.*

SUMMARY OF THE NEW VARIETY

The 'Yellow Star Seedless' is particularly characterized by being a triploid, genetically (and hence commercially) seedless, good fruit size, precocious with stable year-to-year high yields, and an early bearing variety (August/September) in Northern Hemisphere citrus bearing regions. The trees exhibit high levels of tolerance to the malady known as Mal secco, a fungal disease of serious importance in the Mediterranean citrus regions caused by a fungus called *Phoma tracheiphila.*

DETAILED DESCRIPTION

Referring more specifically to the horticultural details of the new and distinct variety of triploid lemon, the following descriptions have been observed on a $4^{th}$ year tree under the ecological conditions prevailing at the origin orchard which is located in Sicily, Italy as well as in Riverside, Calif. Color references are to the Dictionary of Color by Maerz and Paul, First Edition published in 1930. Common colors are also employed.

TREE

Size: Medium, for $4^{th}$ year tree.
*Height.*—10 feet.
*Width.*—8 feet at drip line.
Shape: Upright, growth habit when grown on 'Sour Orange' rootstock.
Growth: Dense; vigorous branches tend to grow out, upward beyond trees' general periphery; abundant axillary and accessory bud development.
Vigor: Strong.
Productivity: Very good for $4^{th}$ year tree with regular bearing; fruit produced predominantly inside the canopy resulting in less fruit scaring.

TRUNK

Immediately above the rootstock interface on 'Sour Orange':
Size: Circumference of 12–16 inches, 18 inches above ground.
Surface texture: Smooth.
Color: 4 year old tree, Andover green (23-E-2).
Lenticels: Many.

BRANCHES

Figure 1:
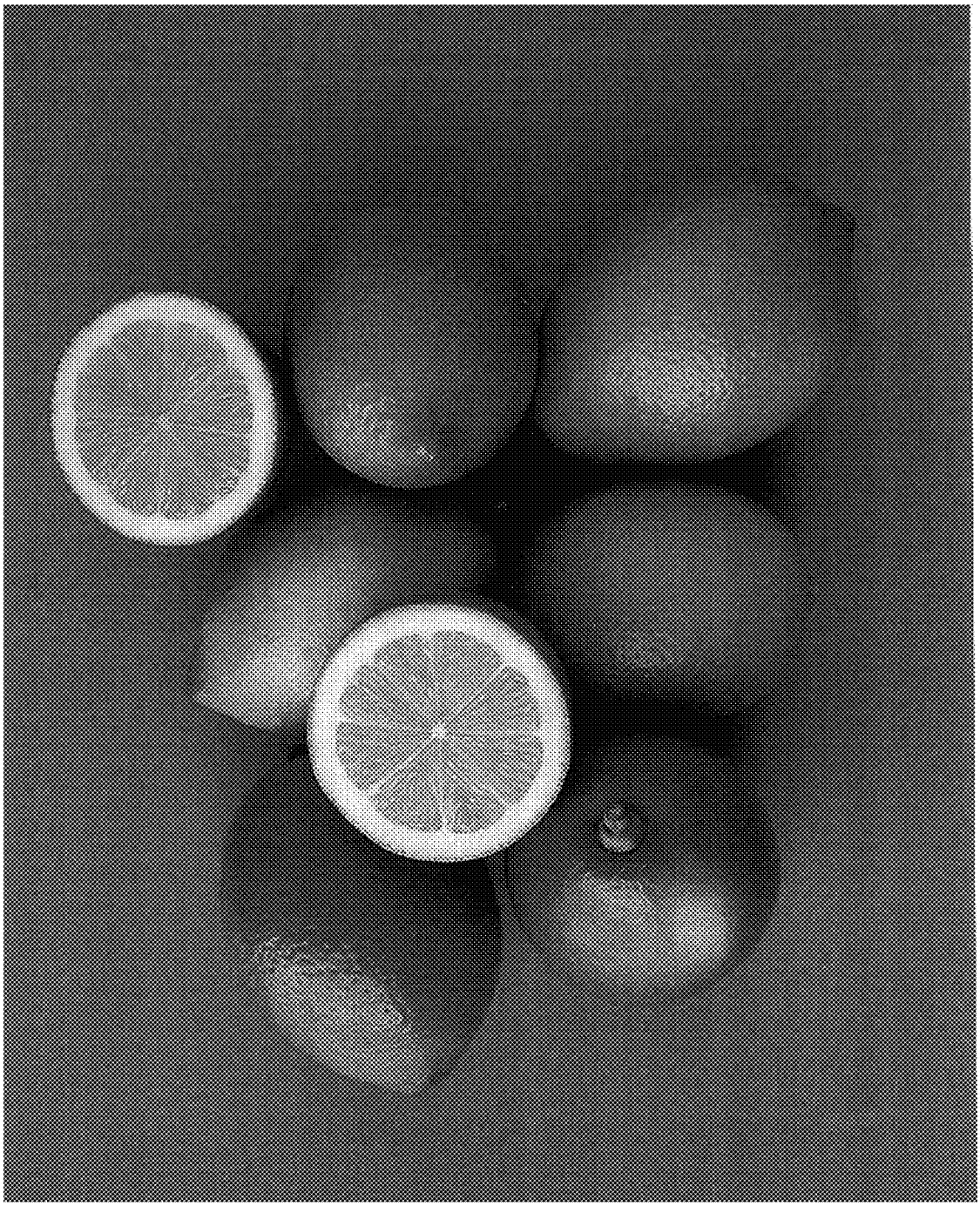
FIG. 1 is a color photograph showing perspective views of several specimens of typical whole fruit, and one transversely cut fruit of the present invention harvested in September 2002.
Figure 2:
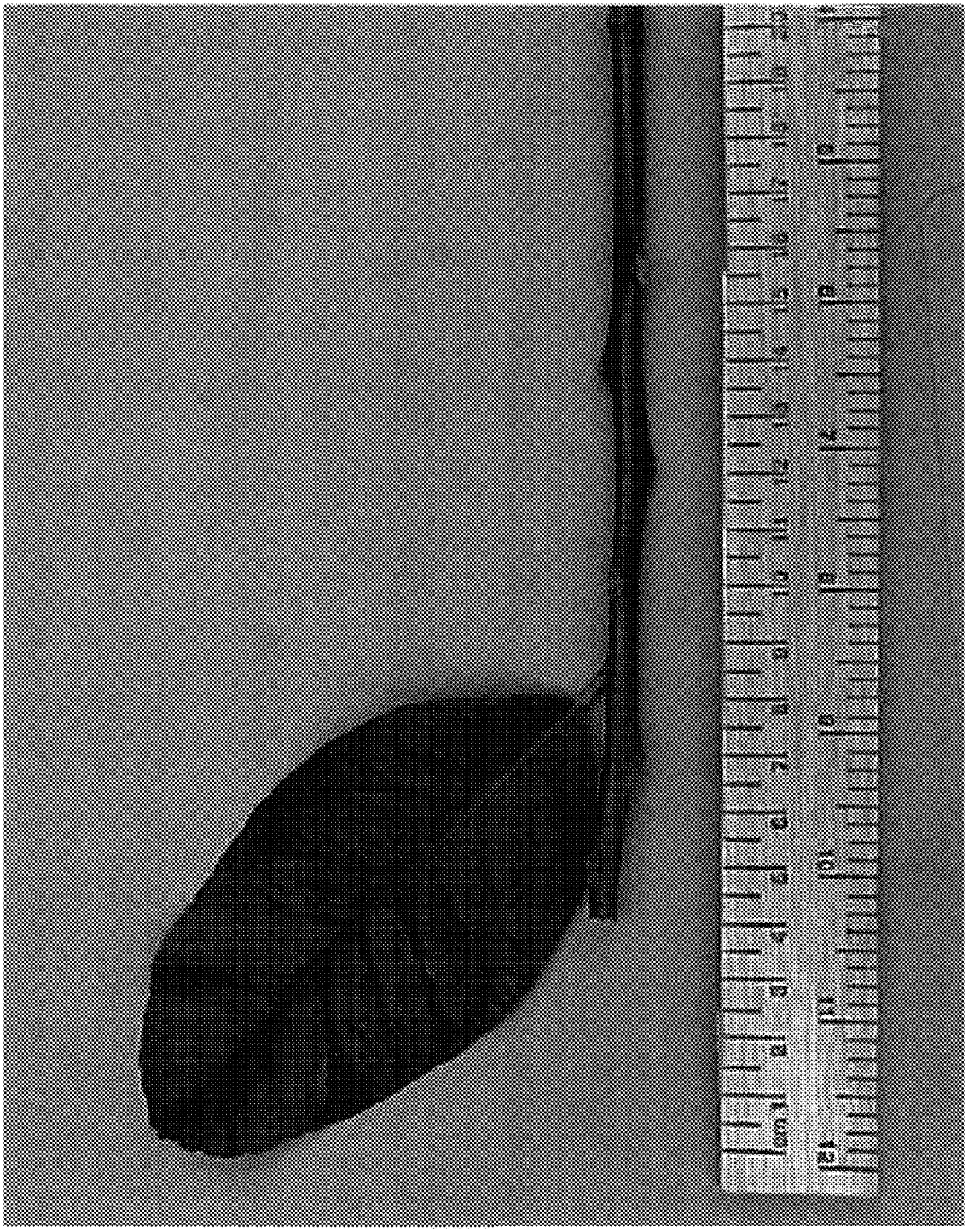
FIG. 2 is a color photograph showing a typical branch from a one year old tree, showing the typical leaf arrangement and minimal thorns of the present invention.
Figure 2A:
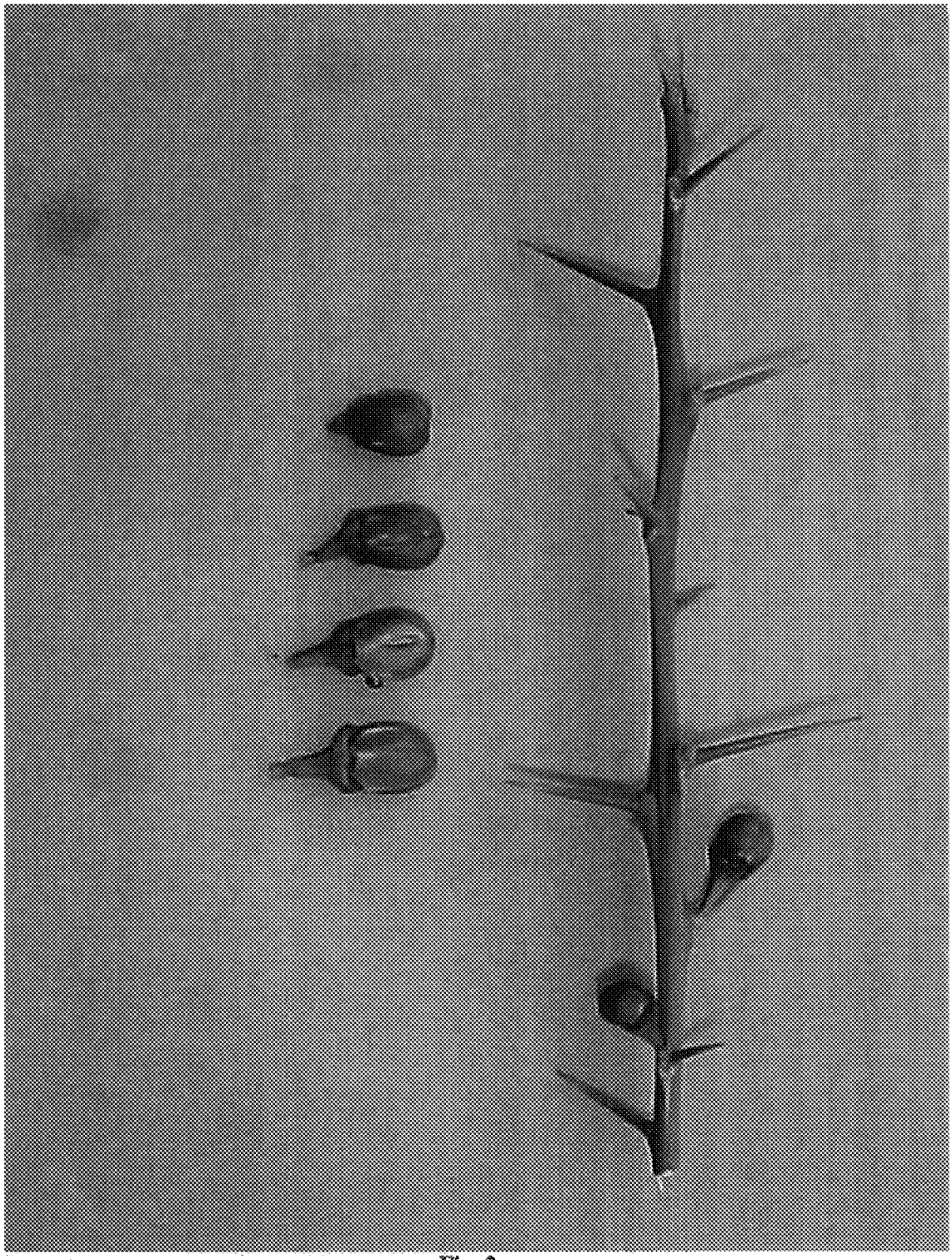
FIG. 2*a* is a color photograph of a juvenile branch showing thorns and flower buds.
Figure 3:
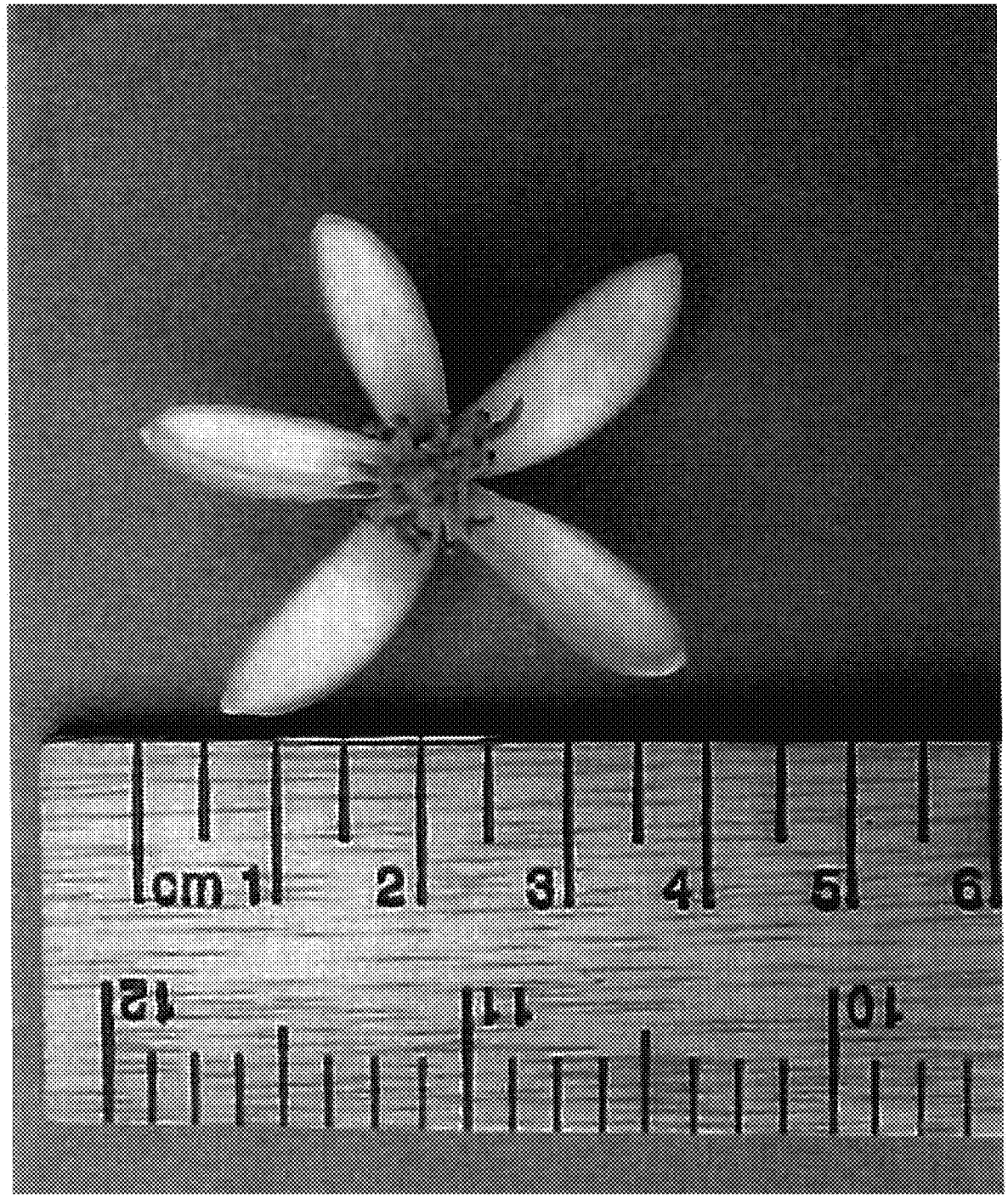
FIG. 3 is a color photograph showing a typical top view of a flower of the present invention.
Figure 4:
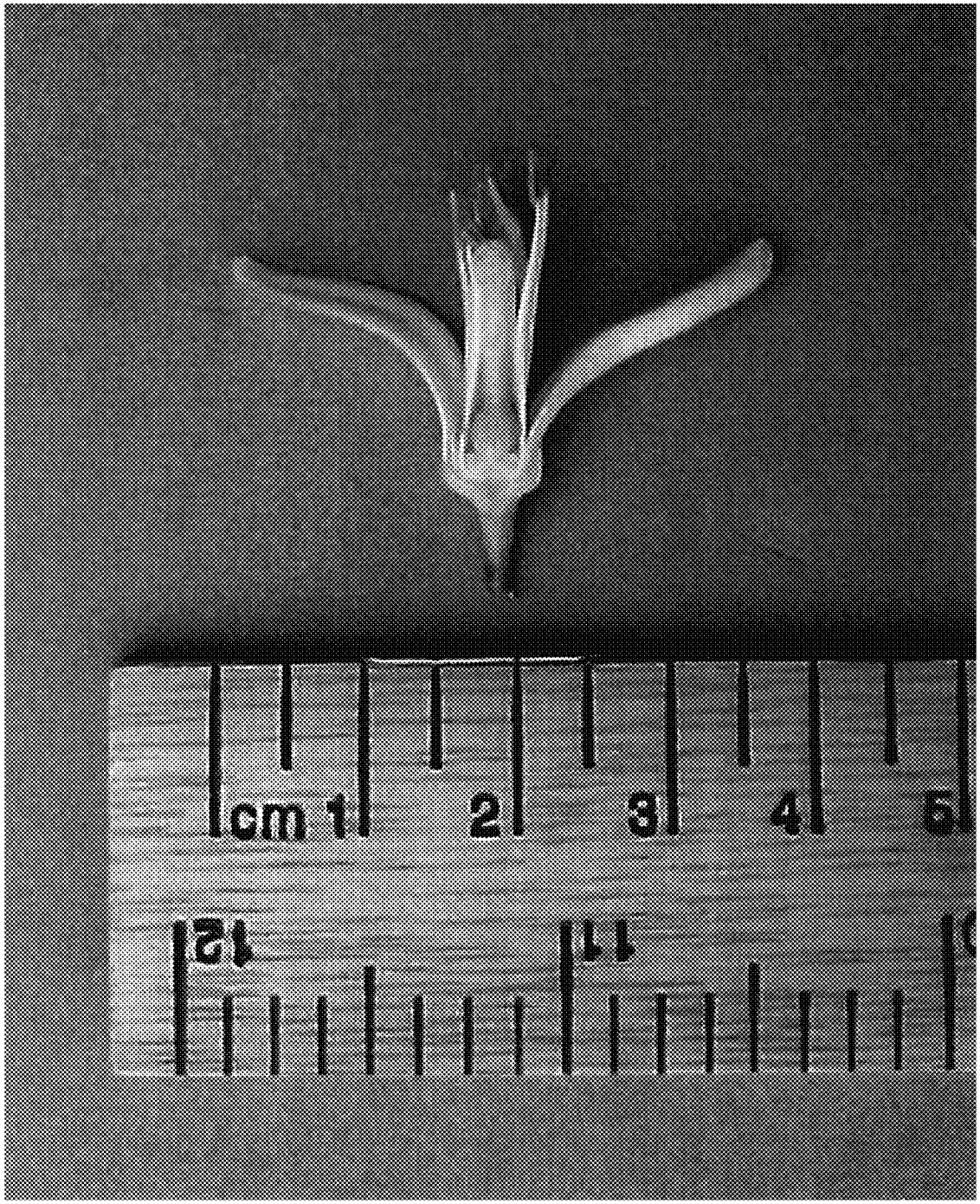
FIG. 4 is a color photograph showing a side sectional view of a typical cut section of the flower of the present invention.
Figure 5:
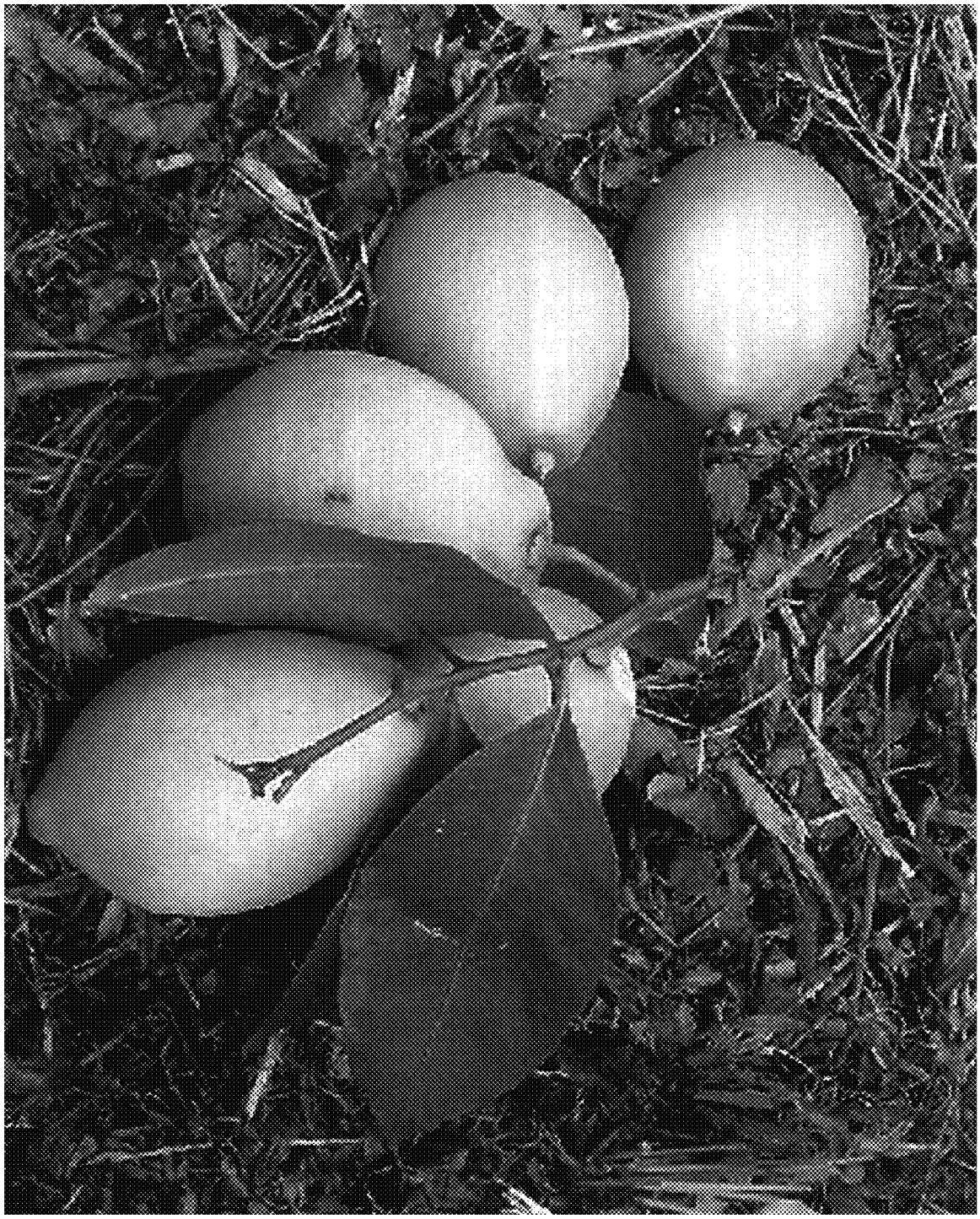
FIG. 5 is a color photograph of the typical fruit arrangement on a branch.
Figure 6:
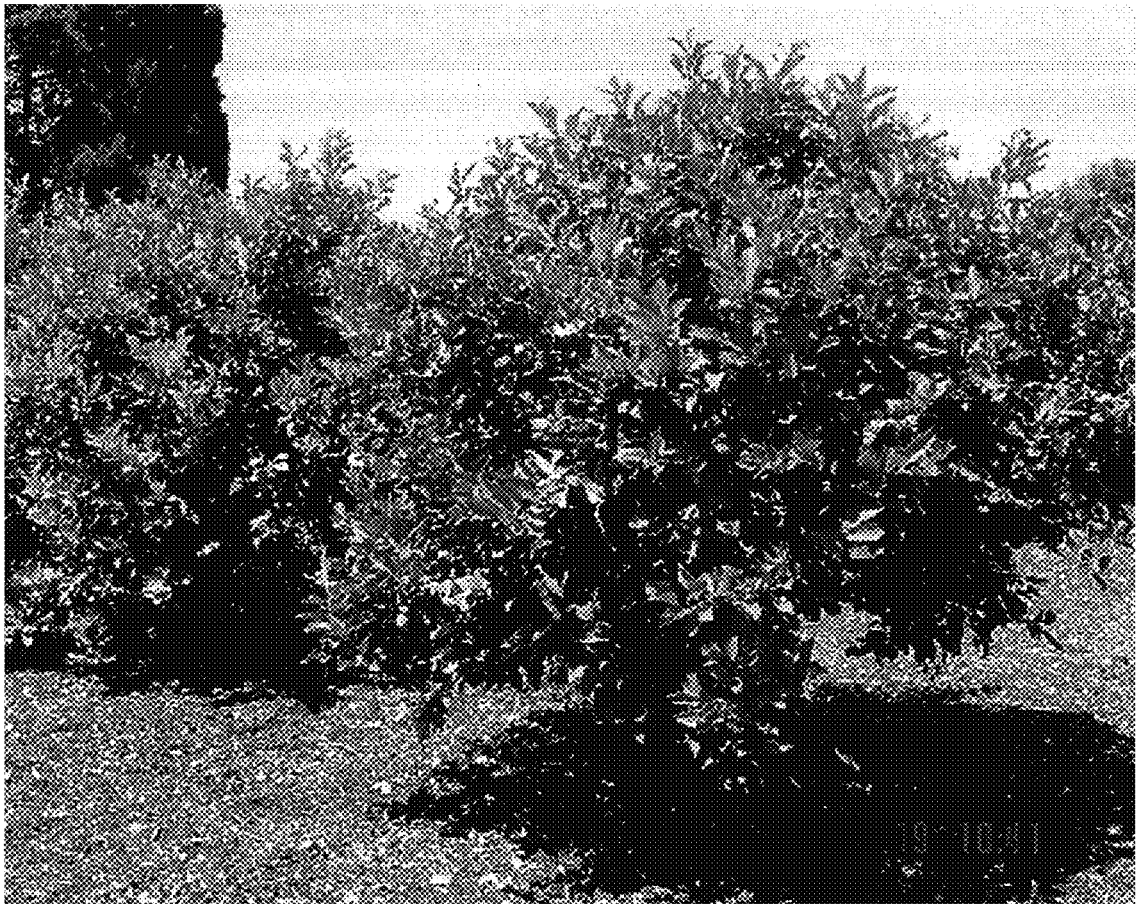
FIG. 6 is a color photograph of a 4 year old bearing tree.

Size: Scaffold (structural) branches, circumference of 10–12 inches; Secondary branches (on which fruit bearing branches are borne) circmference of 4–6 inches.
Angle of branches extending from main trunk: Average between about 30° and about 50°.
Color of branches over 2 years old: Andover green (23-E-2).
Color of branches less than 2 years old: Brunswick green, $LT^P$ (22-L-10).
Thorns: Reduced as tree matures (See FIG. 2). In juvenile branches thorns may be present, with the following dimensions:
*Width at base.*—2–3 mm (0.1–0.12 in.).
*Length.*—10–15 mm (0.4–0.6 in).
*Average width at base.*—2.5 mm(0.1 in); average length: 12 mm (0.5 in). (See FIG. 2*a*).

LEAVES

The leaves are alternate, unifoliate with distinct articulation between the petiole and leaf blade. They exhibit a slight curvate morphology with undulation, and are without basal wings.

Size: Medium.
*Length.*—75–110 mm (3–4.4 in.).
*Width.*—60–70 mm (2.4–2.8 in.).
Texture: Predominantly smooth to slightly pebbled, depressions in the adaxial surface corresponding to vein channels. Abaxial surface has raised leaf veins.
Shape: Elliptically oval to oblong. Approximately transversely and longitudinal symmetrical.
Margin: Smooth serrations at edge.
Apex: Mild crenation to pointed at the apex (mildly acute).
Base: Not elongated.
Edges: Distinctly smoother towards the basal leaf end.
Marginal oil cells: Many 6–10 per linear cm; oil cells are ovoid and smooth.
Color: Mature leaves glossy.
*Upper surface.*—Chrome Green $LT^P$ (22-L-12).
*Lower surface.*—Light Green (20-K-8).
Petioles: No wings (characteristic of true lemon).
*Length.*—Less than 8–12 mm (0.28–0.48 in.).
*Diameter.*—Less than 3 mm (0.12 in.).
*Color.*—Apple green (19-J-6).
Venation: Distinct, pinnately reticulated.
Midvein: Width at base, 1–2 mm (0.04–0.08 in.); Width at apex, 0.3 mm–0.4 mm (0.012–0.016 in.).
*Color.*—Chrome Green $LT^P$ (22-L-12).

FLOWERS

The flowers are large and complete. Flower buds have pink anthocyanin coloration during early development, but lose the most of their pigmentation by anthesis. Flowers are borne in single or multiple clusters and have an average number of stamens (about 20–30) with complete style development. Anther color is pale yellow to yellow. Pollen fertility is very low to sterile as indicated by the observation that less than <0.01% of the pollen grains stained with acetocarmine. The flowers have a sweet pleasing citrus fragrance.

Flower buds:

*Shape.*—10 days prior to anthesis, slightly ovoid, 10 mm (0.4 in.) diameter 1–2 days prior to flowering, elongated cone, 10–12 mm (0.4–0.48 in.) diameter, length — 20–25 mm (0.8–1 in.).

Calyx: 4–5 sepals, fused forming a cup-like calyx.

*Exterior surface color.*—Calliste green (19-L-6). Lobe tips are blunt but with apiculate tips.

Date of normal first bloom:

*Sicily, Italy.*—First bloom: about March 15$^{th}$; end bloom about April 15$^{th}$.

*Riverside, Calif.*—First bloom about April 1$^{st}$, end bloom about April 20$^{th}$.

Flowers: Medium — in clusters of three to five.

*Diameter when fully opened.*—25–40 mm (1–1.6 in.).

*Bloom.*—e.g. quantity — abundant (typical of a lemon) non-alternate bearing.

Petals: 4–5, acute tips.

*Size.*—Medium to large (compared to other citrus species). Length: 15–20 mm (0.6–0.8 in.). Width: 5–8 mm (0.2–0.32 in.).

*Form.*—Narrow, linear, slightly oblong.

*Color.*—Adaxial surface — white (1-A-1). Abaxial surface — White to slightly pink (2-B-1).

*Claws.*—None.

Petal margins: Smooth, pointed at tips (acute).

Pedicel: 4–6 mm (0.16–0.24 in.) average.

*Color.*—Sea green (19-K-6).

Sepals: Color: Glass green (18-F-3).

Stamen: Number: 20–30, with complete style development. Length 10–15 mm.

*Filament.*—White (10-A-1).

*Anthers.*—2–4 mm (0.08–0.16 in.) length; 1–2 mm (0.04–0.08 in.) width.

*Color.*—Aureolin$^{P}$ (10-L-2).

Pistil:

*Stigma.*—Ovoid shape, 3–4 mm (0.12–0.16 in.) diameter; Color: Pineapple (11-J-2).

*Style.*—8–10 mm (0.32–0.4 in.) length; 2–3 mm (0.08–0.12 in.) wide; Color: Sea foam Y (17-C-2).

*Ovary.*—6–8 mm (0.24–0.32 in.) diameter; ovoid shape; Color: Imperial jade (21-L-12).

FRUIT

On grafted trees the first fruit production occurred after two seasons. Internal characteristics: The fruit is commercially seedless in its normal cropping cycle. There is no persistence of the style on the fruit.

Internal characteristics:

Flesh color: Near rind, yellow (18-I-1); Remainder, yellow (18-I-1).

Interior segments: Average of 8 to 10 in number.

Interior segment membranes—Thin.

Pulp vesicles: Medium, 6–8 mm (0.24–0.32 in.) length; 2 mm (0.08 in.) diameter, color: yellow (18-I-1).

The septa: Dorsal slightly convex contoured character.

Juice: Abundant in mature fruit, evenly distributed in sections, typical lemon flavor: rich, with high acid and low sugar, well blended. (pH of 3–3.7). The fruit center is complete without separation. Rind oil cells are medium to large, and occur at a density of approximately 150–200 per cm$^2$.

Oil: 0.6–0.65% (approx. 625 g oil/100 kg fruit).

Glandular layer 2–3 mm (0.08–0.12 in.).

Mesocarp (albedo) 5–8 mm (0.2–0.32 in.).

Axis: 5–6 mm (0.2–0.24 in.) diameter.

Fruit weight: Average of 140 g–160 g (mean of 100 fruit per tree and 5 trees).

Date of maturity: Sicily, Italy: about August 25$^{th}$. Riverside Calif. About September 5$^{th}$.

External characteristics:

Size: Medium.

*Length.*—60–70 mm (2.36–2.76 in.).

*Width.*—50–60 mm (1.97–2.36 in.).

Form: Ovoid.

*Fruit surface.*—Smooth.

Basal (stem end) even to slightly raised.

Base: Diameter 12–14 mm (0.48–0.56 in.).

Stem: Length 10–12 mm (0.4–0.48 in.).

Calyx: diameter 8–12 mm (0.32–0.5 in.).

Apex: Slightly raised, slightly nippled.

Areole: Absent.

Stylar scar: Slight, diameter 1–2 mm (0.04–0.08 in.).

Rind: Surface — smooth.

*Thickness.*—Average 4–8 mm (0.16–0.32 in.).

*Color.*—Shamrock (19-L-12) at first harvest (August) developing to a deep yellow (17-L-1) by the end of November.

Internal fruit quality acceptability occurs approximately one month prior to color change.

The above description of this new variety of lemon is based on the growing conditions prevalent in the Sicily, Italy and in Riverside, Calif.; variations of the usual magnitude, such as differences in maturity date and production, may be due to cultural practices including irrigation, fertilization, pruning, fruit thinning and primary climate changes as well as soil conditions.

Use: fresh market/juice/oil extraction.

Keeping quality: Excellent (stores for 6 month in controlled atmosphere).

First harvest date: Around August 25$^{th}$ in Sicily, Italy. Around September 5$^{th}$ in Riverside, Southern Calif.

Post harvest disorders are similar to existing lemon varieties. In post harvest storage trials under standard controlled atmosphere conditions, the 'Yellow Star Seedless' could be economically stored, with minimal fruit loss for at least 6 months.

Table 1 below compares the fruit skin color, seeds and pollen fertility between fruit harvested from the 'Yellow Star Seedless' as compared to 'Siracusano' Lemon on Sep. 14, 2002. Table 2 below compares the fruit on Oct. 19, 2002:

TABLE 1

| Tree | Fruit skin color (Sep. 14, 2002) | Seeds/fruit* (Sep. 14, 2002) | Pollen fertility** |
|---|---|---|---|
| 'Siracusano' Lemon | Shamrock Gr (19-L-12) | 5–7 | 85% |
| Yellow Star Seedless | Spring Gr (18-J-7) | 0 | <0.01% |

*500 fruit assessed per tree, 5 trees

**Estimated by acetocarmine staining during flowering in April

TABLE 2

| Tree | Fruit skin color (Oct. 19, 2002) | Seeds/fruit* (Oct. 19, 2002) | Pollen fertility** |
|---|---|---|---|
| 'Siracusano' Lemon | Yellow | 7–9 | 85% |
| Yellow Star Seedless | Endive (17-L-3) | 0 | <0.01% |

*500 fruit assessed per tree, 5 trees

**Estimated by acetocarmine staining during flowering in April

Table 3 details some preliminary yield data for grafted trees. Table 4 compares fruit juice and acid content for the 'Yellow Star Seedless' lemon as compared to 'Siracusano' lemons for the 2002–2003 season. Measurements in each case were carried out on 10 fruit per tree and a 5 tree sample giving a total of a 50 fruit sample. Table 5 illustrates a typical picking pattern from the Yellow Star Seedless lemon variety.

TABLE 3

| Typical Yield | | |
|---|---|---|
| Year | Yield | Average Fruit Size |
| Yr 1 | 0 | n/a |
| Yr 2 | 35 kg | 140 g |
| Yr 3 | 75 kg | 154 g |
| Yr 4 | 140 kg | 162 g |

TABLE 4

| | Fruit Acid | | | | | |
|---|---|---|---|---|---|---|
| | 'Yellow Star Seedless' | | | 'Siracusano' Lemon | | |
| Date | Acid (meq/100 g) | TSS (%) | Juice % | Acid (meq/100 g) | TSS (%) | Juice % |
| August 30th | 110 | 9.1 | 31 | 95 | 9.8 | 25 |
| September 30th | 117 | 8.3 | 36 | 104 | 8.7 | 30 |
| October 30th | 114 | 7 | 38.5 | 111 | 7.8 | 31 |
| November 30th | 111 | 6.5 | 41.5 | 109 | 7.1 | 35 |

TABLE 5

| Typical Picking Pattern of the 'Yellow Star Seedless' Lemon in Sicily, Italy | | |
|---|---|---|
| First Pick: | 15% of total | End August |
| Second Pick | 30–40% of total | End September |
| Third Pick | 30% of total | Early November |
| Fourth Pick | 20% of total | January |

What is claimed is:

1. A new and distinct early harvesting variety of seedless lemon tree as described and illustrated called 'Yellow Star Seedless' that is characterized as a triploid having early fruit production from about the end of August through to about January in the citrus areas of Sicily, Italy and Riverside, Calif., the trees coming into bearing by year 3, consistently bearing each year thereafter, and having high tolerance to Mal secco disease, the seedless fruit having typically ovoid shape, an average juice content of about 30% to about 40% at harvest, with smooth skin texture, and having acceptable rind thickness, acid-sugar ratios and color.

* * * * *

UNITED STATES PATENT AND TRADEMARK OFFICE

CERTIFICATE OF CORRECTION

PATENT NO. : PP 17,520 P3
APPLICATION NO. : 11/041066
DATED : March 27, 2007
INVENTOR(S) : Giuseppe Reforgisto Recupero, Giuseppe Russo and Santo Recupero It is certified that error appears in the above-identified patent and that said Letters Patent is hereby corrected as shown below:

Column 1:

Lines 27-28, After "holding/storage" insert --characteristics--

Column 4:

Under "Branches", then "Thorns:":
Kindly delete "Width at base. - 2-3 mm (0.1 - 0.12 in.)" and replace with --Width at base - 2-3 mm (0.08 - 0.12 in.).--

Under "Leaves", then "Petioles":
Kindly delete "Length. - Less than 8-12 mm (0.28-0.48 in.)" and replace with --Length. -Less than 8-12 mm (0.32-0.48 in.).--

Column 5:

Under "Stamen":
After "Length 10-15 mm" insert --(0.4 - 0.6 in.)--

Column 6:

After "Calyx: diameter":
Kindly delete "8-12 mm (0.32-0.5 in.)" and replace with --8-12 mm (0.32-0.48 in.)--

Signed and Sealed this

Twenty-sixth Day of June, 2007

JON W. DUDAS
*Director of the United States Patent and Trademark Office*